United States Patent [19]

Kawasaki et al.

[11] Patent Number: 4,540,702
[45] Date of Patent: Sep. 10, 1985

[54] 2-SUBSTITUTED-4-THIAZOLIDONES

[75] Inventors: Takao Kawasaki, Sayama; Tadashi Tsuchiya, Matsudo; Yoshiaki Osaka, Nagareyama, all of Japan

[73] Assignee: Kureha Kagaku Kogyo Kabushiki Kaisha, Nihonbashi, Japan

[21] Appl. No.: 412,964

[22] Filed: Aug. 30, 1982

Related U.S. Application Data

[63] Continuation-in-part of Ser. No. 162,933, Jun. 25, 1980, abandoned.

[30] Foreign Application Priority Data

Jul. 9, 1979 [JP] Japan ................................. 54-87056
May 23, 1980 [JP] Japan ................................. 55-68506

[51] Int. Cl.$^3$ .................... A61K 31/425; C07D 277/14
[52] U.S. Cl. ..................................... 514/369; 548/186; 548/187
[58] Field of Search ................ 548/186, 187; 424/270

[56] References Cited

U.S. PATENT DOCUMENTS 2,623,048 12/1952 Long et al. ............................ 548/186
4,053,471 10/1977 Krapcho ................................ 548/186

FOREIGN PATENT DOCUMENTS 1345159 1/1984 United Kingdom ................ 548/187

OTHER PUBLICATIONS

Chizhevskaya, Vestsi Akad Navuk Belarus SSR, Ser. Khim. Navuk, (6) 97–102 (1969), Abstract only.
Surrey et al., J. Am. Chem. Soc., vol. 76, pp. 578–580 (1954).
Elderfield, Heterocyclic Compounds, vol. 5, (New York, 1957), pp. 698–699.
Ladnaya et al., Chem. Abstracts, vol. 78, Abstract No. 71977v (1973).
Chizhevskaya et al., Chem. Abstracts, vol. 73, Abstract No. 3834t (1970).
Chemical Reviews, vol. 61, No. 5, p. 470, 1961.
Chemical Abstracts, vol. 89, No. 13, 1978, 9. 25, p. 71, 100017s.

*Primary Examiner*—Alton D. Rollins
*Attorney, Agent, or Firm*—Wegner & Bretschneider

[57] ABSTRACT

Disclosed herein novel compounds, 2-substituted-4-thiazolidones having anti-peptic ulcer activity, and methods for producing the same.

3 Claims, No Drawings

2-SUBSTITUTED-4-THIAZOLIDONES

CROSS-REFERENCE TO RELATED APPLICATION

The present application is a continuation-in-part of U.S. patent application Ser. No. 162,933, filed June 25, 1980, now abandoned.

SUMMARY OF THE INVENTION

In the first aspect of the present invention, there is provided 2-substituted-4-thiazolidone represented by the general formula (I):

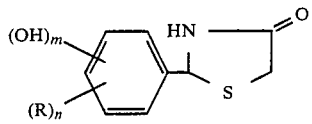

wherein R represents methoxy-, ethoxy-, carboxyl-, methylene-dioxy-, or dimethylamino- and n is an integer of 1 to 3, m is 0 or 1.

In the second aspect of the present invention, there is provided a pharmaceutical composition in dosage unit form, which comprises 2-substituted-4-thiazolidone represented by the general formula (I):

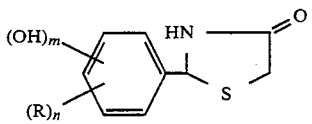

wherein R represents methoxy-, ethoxy-, carboxyl-, methylene-dioxy-, or dimethylamino- and n is an integer of 1 to 3 and m is 0 or 1.

In the third aspect of the present invention, there is provided a process for producing 2-substituted-4-thiazolidone represented by the general formula (I):

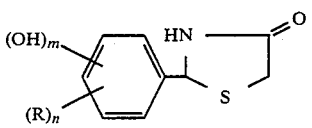

wherein R represents methoxy-, ethoxy-, carboxyl-, methylene-dioxy-, or dimethylamino-, n is an integer of 1 to 3, and m is 0 or 1 comprising the steps of:

(a) reacting a compound represented by the general formula (IV):

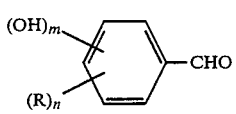

wherein R, n and m represent the same as in the formula (I), with mercaptoacetic acidamide at a temperature of 10° to 50° C. to form an intermediate represented by the general formula (V):

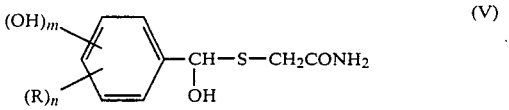

wherein R, n and m represent the same as in formula (I):

(b) successively subjecting intermediate (V) to cyclization at a temperature of 50° to 150° C. thereby obtaining a compound according to formula (I).

DETAILED DESCRIPTION OF THE INVENTION

The present invention relates to novel 2-substituted-4-thiazolidones.

The novel compounds according to the present invention is represented by the following general formula:

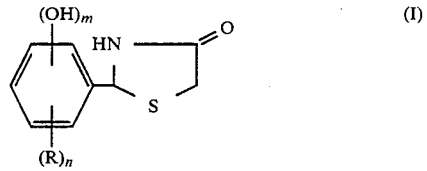

wherein R represents a methoxy group, ethoxy group, carboxyl group, methylenedioxy group or dimethylamino group, and n represents an integer of 1 to 3, and m is 0 or 1.

2-substituted-4-thiazolidones represented by the general formula (I) have excellent anti-peptic ulcer action and also are pharmacologically safe compounds.

There are two kinds of compounds in 2-substituted-4-thiazolidones of the present invention represented by the general formula (I).

The compounds of the present invention are 2-substituted-4-thiazolidone represented by the general formula (II):

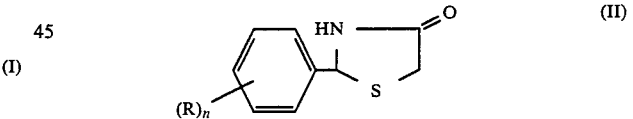

wherein R represents a methoxy-, ethoxy-, carboxyl-, methylene-dioxy- or dimethylamino group and n is an integer of 1 to 3.

2-substituted-4-thiazolidones represented by the general formula (II) according to the present invention (hereinafter referred to as the present compounds) include the following compounds:

2-(2-methoxyphenyl)-4-thiazolidone, 2-(3-methoxyphenyl)-4-thiazolidone, 2-(4-methoxyphenyl)-4-thiazolidone, 2-(2-ethoxyphenyl)-4-thiazolidone, 2-(3-ethoxyphenyl)-4-thiazolidone, 2-(4-ethoxyphenyl)-4-thiazolidone, 2-(2,3-dimethoxyphenyl)-4-thiazolidone, 2-(2,4-dimethoxyphenyl)-4-thiazolidone, 2-(2,5-dimethoxyphenyl)-4-thiazolidone, 2-(3,4-dimethoxyphenyl)-4-thiazolidone, 2-(3,4-methylenedioxyphenyl)-4-thiazolidone, 2-(4-dimethylaminophenyl)-4-thiazolidone, 2-(2-carboxyphenyl)-4-thiazolidone, and 2-(3,4,5-trimethoxyphenyl)-4-thiazolidone.

The other compounds of the present invention are 2-substituted-4-thiazolidone represented by the general formula (III):

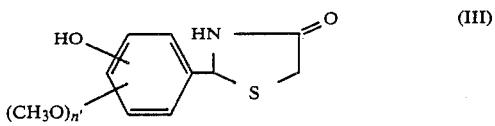

wherein n' is an integer of 1 to 2.

2-substituted-4-thiazolidones represented by the general formula (III) according to the present invention (hereinafter referred to as the present compounds) include the following compounds:

2-(3,5-dimethoxy-4-hydroxyphenyl)-4-thiazolidone and 2-(3-methoxy-4-hydroxyphenyl)-4-thiazolidone.

The melting points, appearance and elementary analytical compositions of the present compounds are shown in Table 1.

into reaction for one to 10 hours while removing water formed during the reaction, or (b) the reaction is carried out in the initial stage at a relatively low temperature of 10° to 50° C. for one to 60 minutes, preferably 2 to 10 minutes and then successively at 50° to 150° C. for 0.5 to 10 hours.

In the sub-method (b), the reaction is carried out in two consecutive stages, that is, in the first stage, an intermediate compound represented by the following general formula (V):

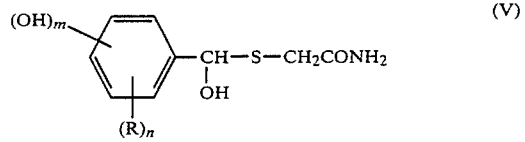

wherein R, m and n mean the same as in the above, and in the second stage, an objective thiazolidone is formed

TABLE 1

| | Compounds according to present invention | | | | | |
| --- | --- | --- | --- | --- | --- | --- |
| | Melting point | | Elementary Analytical Composition (%) | | | |
| Compound | (°C.) | Appearance | C | H | N | S |
| 2-(2-methoxyphenyl)-4-thiazolidone | 174–175 | colourless micro-needle-like crystals | 57.38 (57.40) | 5.33 (5.30) | 6.71 (6.70) | 15.28 (15.32) |
| 2-(4-methoxyphenyl)-4-thiazolidone | 128.5–129.5 | colourless micro-needle-like crystals | 57.38 (57.40) | 5.28 (5.30) | 6.68 (6.70) | 15.32 (15.32) |
| 2-(2-ethoxyphenyl)-4-thiazolidone | 142–143 | colourless prisms | 59.23 (59.17) | 5.80 (5.87) | 6.29 (6.27) | 14.40 (14.36) |
| 2-(2,5-dimethoxyphenyl)-4-thiazolidone | 157–158 | colorless needle-like crystals | 55.25 (55.21) | 5.50 (5.48) | 5.82 (5.85) | 13.36 (13.40) |
| 2-(3,4-dimethoxyphenyl)-4-thiazolidone | 184.5–186 | colourless micro-needle-like crystals | 55.24 (55.21) | 5.50 (5.48) | 5.83 (5.85) | 13.36 (13.40) |
| 2-(3,4-methylenedioxyphenyl)-4-thiazolidone | 163.5–165 | colourless needle-like crystals | 53.62 (53.80) | 4.10 (4.06) | 6.30 (6.27) | 14.35 (14.36) |
| 2-(2-carboxyphenyl)-4-thiazolidone | 205–207 | colourless micro-needle-like crystals | 53.80 (53.80) | 3.90 (4.06) | 6.10 (6.27) | 14.32 (14.36) |
| 2-(4-hydroxy-3,5-dimethoxyphenyl)-4-thiazolidone | 105–106 | pale-yellow needle-like crystals | 51.90 (51.75) | 5.23 (5.13) | 5.45 (5.49) | 12.60 (12.56) |
| 2-(4-ethoxyphenyl)-4-thiazolidone | 163.5–165 | colourless micro-needle-like crystals | 59.15 (59.17) | 5.87 (5.87) | 6.29 (6.27) | 14.40 (14.36) |
| 2-(2,3-dimethoxyphenyl)-4-thiazolidone | 133–134.5 | colourless plate-like crystals | 55.24 (55.21) | 5.47 (5.48) | 5.85 (5.85) | 13.38 (13.40) |
| 2-(4-dimethylaminophenyl)-4-thiazolidone | 161–162.5 | colourless needle-like crystals (from methanol) | 59.41 (59.43) | 6.38 (6.35) | 12.59 (12.60) | 7.18 (7.20) |
| 2-(3,4,5-trimethoxyphenyl)-4-thiazolidone | 159–160 | colourless needle-like crystals (from methanol) | 53.53 (53.53) | 5.60 (5.58) | 5.18 (5.20) | 11.87 (11.90) |

N.B.: The parenthesized figures in Elementary Analytical Composition show the theoretical values based on the molecular formula of each compound.

The present compounds are possibly produced by either of the following two methods (1) and (2):

(1) An aldehyde represented by the general formula,

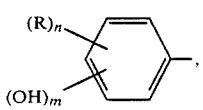

wherein R, m and n mean the same as in the formula (I), is brought into reaction with an equimolar or a little excessive amount of mercaptoacetic acidamide in an inert solvent such as benzene, toluene and xylene. In the reaction, there are two sub-methods as follows:

(a) at a temperature of 50° to 150° C., usually at the boiling point of the solvent, the reactants are brought without formation of any by-products, by cyclization of the intermediate compound. Accordingly, the present compound is possibly produced at a high yield due to the high formation rate of the intermediate compound by adopting the sub-method (b), and it is extremely advantageous industrially as compared to the sub-method (a). For reference, the reaction formulae in the both sub-methods (a) and (b) are as follows:

According to (a):

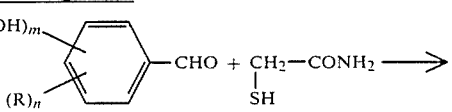

-continued

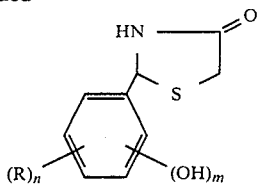

According to (b):

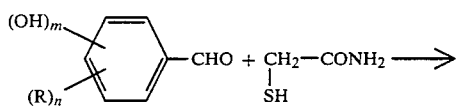

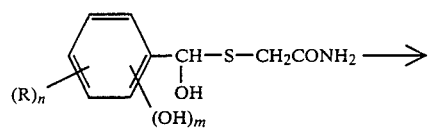

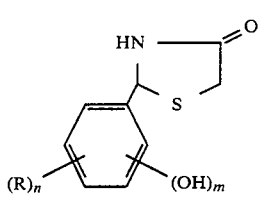

In addition, since the rate of formation of the intermediate compound in the sub-method (b) is reduced with the raise of the temperature of reaction, the temperature during the initial stage of the reaction is preferably kept as low as possible within the range above-mentioned.

(2) A method in which the aldehyde represented by the above-mentioned general formula (IV),

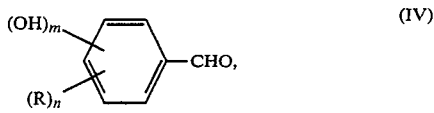

(IV)

is brought into reaction with an equimolar or a little excessive amount of thioglycolic acid or its ester and an ammonium compound, preferably ammonium carbonate in an inert solvent: By this method, at a temperature of 50° to 150° C. for one to 10 hours, an objective thiazolidone is obtained. Since a vigorous bumping phenomenon is frequently experienced in the course of the above-mentioned reaction, a finely pulverized inorganic salt, for instance, magnesium sulfate is preferably added in advance in the reaction system to avoid the bumping.

In the next place, the anti-peptic ulcer action of the present compound is explained. It has been found that the present compound has a specifically strong anti-ulcer action with low acute- and chronic toxicities, and substantially without any effect on cardiovascular system and accordingly, the present compound is possibly utilized as an anti-peptic ulcer medicine.

Originally, the peptic ulcer is the collapsed weakened part of the gastric or enteric mucosa by the action of aggressive factors such as hydrochloric acid and pepsin in the gastric juice, and although the slight cases of peptic ulcer are curable after 3 to 4 months' hospitalization and treatment, the serious cases are accompanied by hemorrhage and perfolation to be chronic.

Although the abnormalities in the autonomic nerve system and the mucosal blood flow due to the physical and mental stresses are considered to be the etiological cause of the peptic ulcer, since the internal organs themselves are under the complexed control of the nerves and hormones, it is practically impossible to interpret the etiology of the peptic ulcer monistrically.

Hitherto, as an anti-peptic ulcer medicine, sodium hydrogen carbonate, aluminum salts and magnesium salts have been administered in the meaning of neutralizing the hydrochloric acid. However, these medicines only temporarily neutralize the acid to alleviate the pain and do not accelerate the substantial cure of the ulcer.

Although various anti-ulcer medicines based on the presumed cause of the ulcer have been developed including the medicines suppressing autonomic nerve, that is, so-called anti-choline agents, the agents repairing the damaged tissue and the agents improving the blood flow, these agents are not yet sufficient in view of their effectiveness or of their side-effects.

For instance, carbenoxolon sodium, presently commercially as an anti-peptic ulcer medicine, has been broadly used due to its excellent accelerating effect on the ulcer-curing, however, the substance has an aldsterone-like side-effect to cause hypertension and weakening of muscular function when taken continuously. Also, the anti-choline agents have a severe side-effect of blocking the parasympathetic nerve system to cause the symptoms such as mydriasis and thirst and it has been reported that their effect of accelerating the ulcer-curing is low.

Since it generally takes a long time period to cure the peptic ulcer, there are many cases where the administration of an anti-peptic ulcer medicine is continued for a long time period on an average of 100 to 150 days, and accordingly, it is required that the anti-peptic ulcer medicine is highly safe as well as highly effective in curing.

The important problem in developing a new anti-peptic ulcer medicine is in the screening system of the candidate anti-peptic ulcer medicines. Hitherto, the evaluation of candidate anti-peptic ulcer medicines has been carried out based on their prophylactic effect against an acute peptic ulcer such as Shay's ulcer and peptic ulcer due to aspirin or indomethacin.

However, what extent does the result of screening carried on such models of peptic ulcer reflect the curing effect in human peptic ulcer of the candidate medicine has not been sufficiently elucidated.

The inventors of the present invention, taking into account of these situations, added to the method of evaluation the effect of accelerating the curation of the peptic ulcer by orally administering the present compound and a commercialized anti-peptic medicine, respectively to rats to which duodenal peptic ulcer due to acetic acid (refer to Okabe, 1971) considered to be most closely resembling to human peptic ulcer has been artificially formed.

ANTI-PEPTIC ULCER EFFECT OF THE PRESENT COMPOUND

According to the conventional method of evaluation, for instance, the test carried out on rats with their pylorus ligated following Shay et al. (1945), the present compound showed a rate of suppressing the occurrence of peptic ulcer of 70 to 90% at an intraperitoneal administration of 100 mg/kg whereas a commercialized anti-peptic ulcer medicine, gefarnate, showed the rate of suppression of only about 11% at the same dose level.

Moreover, in the test method using rats artificially suffering from peptic ulcer due to acetic acid which is said to be the most closely resembling to human peptic ulcer (refer to Okabe, 1971), the present compound showed a rate of curing of 60 to 90% at a dose rate of 100 mg/kg., whereas the agent, gefarnate, showed a rate of curing of only 23% at the same dose level.

The evaluation according to the method of using rats artificially contracted to peptic ulcer induced by acetic acid is explained later in Example 6.

In this connection, the experimental model of artificial peptic ulcer on rats has been highly evaluated internationally because the thus formed ulcer is scarcely curable in nature and the histopathological changes occurring at the ulcer region closely resemble to those of human chronic peptic ulcer, as a method for screening candidate anti-peptic ulcer medicines as compared to the method of forming ulcer by cauterization (refer to Skoryna, 1958) and the method of forming ulcer by administering cortizone on the clamped organ (refer to Umehara, 1965).

In addition, the present compound shows superior effects to the effects of commercialized anti-peptic ulcer on the evaluation by the hitherto broadly utilized effective methods for clinically screening candidate anti-peptic ulcer medicines such as the method of inducing ulcer by stress and the method of inducing ulcer by aspirin.

The anti-peptic ulcer effect of the present compound is concretely shown in Examples 5 and 6 described later.

In the next place, in order to confirm the adaptability of the present compounds as a medicine, the results of their sub-acute toxicity test carried out on experimental animals are shown as follows:

SUB-ACUTE TOXICITY TEST

Experimental animals: Both sexes of Sprague-Dowley rats of five weeks after birth, each weighing 110 to 150 g.

Rearing method: Each five males and five females (consisting a group) were respectively kept in a wire-net cage at a room temperature of 22° to 24° C. and RH of 60 to 70% for 3 months with diets and water ad lib.

Administration of the present compound: Finely pulverized 2-(3,4-dimethoxyphenyl)-4-thiazolidone, as a representative of the present compounds, was mixed with the diet (powdery) at a rate of 0.4% by weight and taken ad lib. for 3 months. The mean intake of the present compound was 400 mg/kg/day.

Determinations: The intake of diets was once every other day, the body weight was once a week, and the ulinalysis for sugar, protein, pH and occult blood was once a month determined. After 3 month-rearing, blood was examined, and the sacrificed animals were autopsied to examine the abnormality. The organs were fixed with formaldehyde and then burried in paraffin to prepare the tissue sections stained with hematoxylin-eosin to be examined under a microscope. The results of the sub-acute toxicity test were as follows:

Intake of diet: not abnormal, no difference was observed to that of control group.

Body weight gain: not abnormal, no difference was observed to that of control group.

Mortality: as above.

Results of ulinalysis: as above.

Results of blood examination: as above.

Findings on autopsy and histological examination: as above.

In addition, according to the results of acute toxicity tests using rats and mice as experimental animals, $LD_{50}$ p.o. was larger than 5 g/kg on rat and mouse, and $LD_{50}$ i.v. was larger than 1.5 g/kg on rat and mouse.

As has been described, the present compound is extremely high in safety and accordingly, it is said to be safely administered to human cases as an anti-peptic ulcer medicine. Since the present compounds are colourless and tasteless or a little bitter in taste, and their stability is extremely high without any change after storing at an open conditions at a room temperature, their adaptability as an anti-peptic ulcer medicine is possibly said to be remarkably high.

The present compound is applicable as a medicinal preparation with a medically acceptable carrier. The type and forms as the medicinal preparations containing one of the present compounds are possibly tablets, sugar-coated tablets, pills, capsules, powders, granules, troches, liquid preparations, suppositories, injections, etc.

In addition, as a carrier thereof, lactose, sucrose, sorbitol, mannitol, potato-starch, corn-starch, amyropectine, other various starches, derivatives of cellulose, for instance, carboxymethylcellulose, methylcellulose, gelatin, magnesium stearate, calcium stearate, polyvinyl alcohol, polyethylene glycol wax, gum arabic, talk, titanium dioxide, vegetable oil such as olive oil, peanut oil and sesame oil, paraffin oil, neutral fatty bases, ethanol, an aqueous physiological saline solution, sterilized water, glycerol, colouring agents, seasonings, thickening agents, stabilizers, isotonic agents and buffer solutions are possibly mentioned.

The content of the one of the present compounds in the medicinal preparations is 0.1 to 90% by weight of the preparation, preferably 1 to 60% by weight of the preparation.

The clinical dose rate of one of the present compounds is 60 to 6,000 mg/60 kg body weight/day, preferably, 600 to 3,000 mg/60 kg body weight, and usually the daily amount is administered after dividing into three equal portions, that is, it is administered three times a day. The route of administration may be oral or injectional, however, in cases of long term administration, oral administration is preferable.

The followings are the more concrete explanation of the present invention while referring to Examples, however it should be understood that the scope of the present invention is never restricted to Examples shown as follows:

SYNTHETIC EXAMPLES OF THE PRESENT COMPOUNDS

EXAMPLE 1

Synthesis of 2-(2-methoxyphenyl)-4-thiazolidone represented by the following formula:

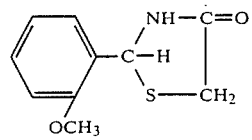

A mixture of 13.6 g (0.1 mol) of o-anisaldehyde, 9.1 g (0.1 mol) of thioglycolic acidamide and 150 ml of benzene was stirred for 3 minutes while heating the mixture to a temperature of 45° C. Then, the heating was stopped and the stirring was continued until the temperature of the mixture became to room temperature. After stirring the mixture for an additional two hours at room temperature, the mixture was heated under a reflux condenser for 2 hours. After cooling the mixture to room temperature, the thus separated crystals were collected by filtration and were recrystallized from benzene. The object, 19.4 g of colourless micro-needle-like crystals, was obtained at a yield of 93%, with a melting point of 174° to 175° C. The elementary analytical composition found and calculated as $C_{10}H_{11}NO_2S$ is shown in Table 1.

EXAMPLE 2

Synthesis of 2-(4-ethoxyphenyl)-4-thiazolidone represented by the following formula:

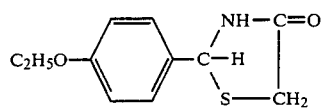

A mixture of 15.0 g (0.1 mol) of p-ethoxybenzaldehyde, 11.0 g (0.12 mol) of thioglycolic acid, 5.8 g (0.6 mol) of ammonium carbonate and 200 ml of benzene was heated at a temperature of 80° C. under a reflux condenser for 5 hours while removing the distilling water by utilizing a specifically attached apparatus of Dean-Stark.

After filtering the reaction mixture while hot and treating with activated carbon, the thus treated mixture was condensed to 100 ml and cooled to separate crystals. By recrystallizing the crystals from benzene, the object, colourless micro-needle-like crystals amounting to 11.6 g at a yield of 52% were obtained, melting at 163.5° to 165° C. The elementary analytical compositions found and calculated based on the molecular formula of $C_{11}H_{13}NO_2S$, respectively, are shown in Table 1.

EXAMPLE 3

Synthesis of 2-(2,3-dimethoxyphenyl)-4-thiazolidone represented by the following formula:

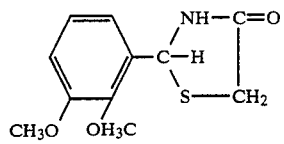

A mixture of 16.6 g (0.1 mol) of 2,3-dimethoxybenzaldehyde, 11.0 g (0.12 mol) of thioglycolic acid, 5.8 g (0.6 mol) of ammonium carbonate, 7 g of magnesium sulfate and 200 ml of benzene was heated under a reflux condenser for 7 hours, and by filtering the reaction mixture while hot, and cooling the filtrate to ordinary temperature, crystals separated out.

After collecting the crystals by filtering and recrystallizing the crystals from benzene, the object, consisting of plate-like colourless crystals, was obtained in an amount of 18.8 g at a yield of 79%, melting at 133° to 134.5° C. The elementary analytical compositions found and calculated from the molecular formula of $C_{11}H_{13}NO_3S$, respectively are shown in Table 1.

EXAMPLE 4

Synthesis of 2-(3,4,5-trimethoxyphenyl)-4-thiazolidone represented by the following formula:

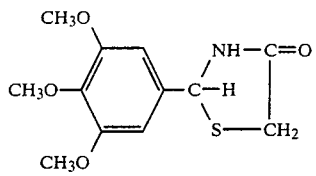

(a) 3,4,5-trimethoxybenzaldehyde (12.5 g) and thioglycolic acidamide (6.4 g) were added to 150 ml of benzene and the mixture was heated under a reflux condenser for 5 hours and then the reaction mixture was treated with activated carbon. The thus treated mixture was condensed to dryness and the residue was recrystalized from hot benzene to obtain colourless needle-like crystals in an amount of 13.5 g corresponding to a yield of 79%, melting at 159° to 159.7° C. (b) A mixture of 12.5 g of 3,4,5-trimethoxybenzaldehyde, 6.5 g of thioglycolic acid, 4 g of ammonium carbonate and 150 ml of benzene was heated at a temperature of 80° C. under a reflux condenser for 5 hours while removing the distilling water by a specifically attached apparatus of Dean-Stark. A phenomenon of bumping was observed during the heating. The reaction mixture was then filtered while hot, and after treating with activated carbon the filtrate was condensed to separate crystals. The separated crystals were recrystallized from hot benzene to obtain 9.6 g of the object consisting of colourless needle-like crystals at a yield of 54%, melting at 159° to 160° C.

(c) A mixture of 12.5 g of 3,4,5-trimethoxybenzaldehyde, 6.5 g of thioglycolic acid, 4 g of ammonium carbonate, 5 g of magnesium sulfate and 150 ml of benzene was heated at a temperature of 80° C. for 5 hours under a reflux condenser while removing the distilling water by a specifically attached apparatus of Dean-Stark. The reaction mixture was filtered while hot and after treating with activated carbon, the filtrate was condensed to separate crystals. By recrystallizing the thus separated crystals from hot benzene, a product amounting to 14.6 g was obtained at a yield of 85%, consisting of colourless needle-like crystals.

Anti-peptic ulcer activity of the present compound

EXAMPLE 5

Effect of one of the present compounds against the peptic ulcer formed by ligating the pylorus artificially on rats:

Each male rat of a group consisting of 10 animals, weighing 180 to 200 g, after 48 hours' fasting, was subjected to ligature at its pyloric part under the anesthesia by ether following the method of Shay et al. (refer to Gastroenterology, Vol. 5, 43, 1945). Just after the ligature, each of the present compounds suspended in an aqueous physiological saline solution was injected into each rat's abdominal cavity at a dose rate of 100 mg/kg body weight, the control group being injected with an aqueous physiological saline solution. After keeping the rats at a state of fasting without taking water for 15 hours, the rats were sacrificed by ether and their stomachs were removed to examine under a microscope for autopsy. The longitudinal and horizontal lengths of the thus formed peptic ulcer were determined and expressed by the product (mm²), and the total sum of the products was represented as the coefficient of ulcer. The results are shown in Table 2.

The rate of suppression of peptic ulcer (%) is expressed by the ratio of the difference between the coefficient of peptic ulcer of control group and the coefficient of peptic ulcer of the treated group to the coefficient of peptic ulcer of control group multiplied by 100.

TABLE 2

Coefficient of peptic ulcer and rate of curation of peptic ulcer by the present compounds Dose rate: 100 mg/kg/day

| Compound | Coefficient of peptic ulcer (mm²) | Rate of suppression of peptic ulcer (%) |
|---|---|---|
| 2-(2-methoxyphenyl)-4-thiazolidone | 5.3 | 87.4 |
| 2-(3-methoxyphenyl)-4-thiazolidone | 5.5 | 86.0 |
| 2-(4-methoxyphenyl)-4-thiazolidone | 13.4 | 68.1 |
| 2-(2-ethoxyphenyl)-4-thiazolidone | 7.6 | 81.9 |
| 2-(2,3-dimethoxyphenyl)-4-thiazolidone | 8.8 | 82.9 |
| 2-(2,5-dimethoxyphenyl)-4-thiazolidone | 9.4 | 79.0 |
| 2-(4-dimethylaminophenyl)-4-thiazolidone | 10.5 | 75.0 |
| 2-(2-carboxyphenyl)-4-thiazolidone | 8.5 | 79.8 |
| 2-(3,4-dimethoxyphenyl)-4-thiazolidone | 3.4 | 91.9 |
| 2-(3,5-dimethoxy-4-hydroxyphenyl)-4-thiazolidone | 7.6 | 81.9 |
| 2-(3,4,5-trimethoxyphenyl)-4-thiazolidone | 6.5 | 85.8 |
| Gefarnate (See footnote) | 37.4 | 10.9 |
| Control | 42.0 | — |

Gefarnate: 3,7-dimethyl-2,6-octadienyl 5,9,13-trimethyl-4,8,12-tetradecatrienoate

TABLE 3

Coefficient of peptic ulcer and rate of curation of peptic ulcer by the present compounds Dose rate: 100 mg/kg/day

| Compound | Coefficient of peptic ulcer (mm²) | Rate of curation of peptic ulcer (%) |
|---|---|---|
| 2-(2-methoxyphenyl)-4-thiazolidone | 1.5 | 80.0 |
| 2-(3-methoxyphenyl)-4-thiazolidone | 2.0 | 73.3 |
| 2-(4-methoxyphenyl)-4-thiazolidone | 3.1 | 58.7 |
| 2-(2-ethoxyphenyl)-4-thiazolidone | 1.8 | 76.0 |
| 2-(2,3-dimethoxyphenyl)-4-thiazolidone | 1.3 | 82.7 |
| 2-(2,5-dimethoxyphenyl)-4-thiazolidone | 2.6 | 65.3 |
| 2-(4-dimethylaminophenyl)-4-thiazolidone | 2.4 | 88.0 |
| 2-(2-carboxyphenyl)-4-thiazolidone | 3.0 | 60.0 |
| 2-(3,4-dimethoxyphenyl)-4-thiazolidone | 1.5 | 80.0 |
| 2-(3,5-dimethoxy-4-hydroxyphenyl)-4-thiazolidone | 2.4 | 88.0 |
| 2-(3,4,5-trimethoxyphenyl)-4-thiazolidone | 1.4 | 82.1 |
| Gefarnate (See footnote) | 5.8 | 22.7 |
| Control | 7.5 | — |

Gefarnate: 3,7-dimethyl-2,6-octadienyl 5,9,13-trimethyl-4,8,12-tetradecatrienoate

EXAMPLE 6

The effect of the present compound on the peptic ulcer induced by acetic acid artificially Following the method of Okabe et al. (refer to Amer. J. Dig. Dis., Vol. 16, 277, 1971), each male rat weighing 240 to 260 g of a group consisting of 15 animals was subjected to laparotomy under ether-anesthesia and a metal circular frame was put on a part of the serosa at the distance of 5 to 7 mm from the duodenal pylorus and 0.06 ml of glacial acetic acid was poured on the circular part of the frame. After 30 seconds, the acetic liquid was removed and the frame was also removed. Each of the present compounds suspended in an aqueous 0.5% CMC solution was orally administered to the rat from after 3 days of the operation three times a day for consecutive 10 days, rats of control group being given the aqueous 0.5% CMC solution. After ending the administration, the rats were sacrificed by ether, their duodenum being removed to be examined under a microscope for autopsy. The longitudinal and horizontal lengths of the thus formed ulcer were determined and the product of the lengths expressed by mm² was recorded as the coefficient of peptic ulcer. The results are shown in Table 3. The rate of curation of peptic ulcer, in this Example is calculated by the same manner as the rate of suppression of peptic ulcer in Example 5.

EXAMPLE 7

Suppressive action of the present compound on gastric secretion

Groups of male rats (a group consisted of 10 animals) were subjected to pyloric ligature under etherization after fasting for 24 hours, and each of the compounds to be tested was administered intraduodenally as an emulsion or suspension in an aqueous 0.5% by weight solution of sodium carboxymethylcellulose just after ligation. After 4 hours of the laparotomy, the stomach of each rat was extirpated under etherization, and the amount of gastric juice in the stomach was measured. The results are shown in Table 4.

TABLE 4

Suppression on gastric secretion by intraduodenal administration of the present compound Amount of administration: 200 mg/kg

| Compound | Amount of gastric juice (ml) | Rate of suppression (%) |
|---|---|---|
| 2-(2-methoxyphenyl)-4-thiazolidone | 4.0 | 40.2 |
| 2-(2-ethoxyphenyl)-4-thiazolidone | 4.3 | 35.8 |
| 2-(2,3-dimethoxyphenyl)-4-thiazolidone | 3.7 | 44.7 |
| 2-(2,5-dimethoxyphenyl)-4-thiazolidone | 3.5 | 32.8 |
| 2-(3,4-dimethoxyphenyl)-4-thiazolidone | 3.3 | 50.7 |
| Control (administered only with CMC*) | 6.7 | 0.0 |
| Gafarnate (comparative, refer to Table 2) | 6.5 | 2.9 |

Note:
*CMC: an aqueous 0.5% by weight solution of sodium carboxymethylcellulose

As are seen in Table 4, each of the present compounds showed an effect of suppression of gastric secretion amounting to 32.8 to 50.7% at a dose rate of 200 mg/kg body weight, and the results suggested that at least a part of the anti-peptic ulcer function of the present compound depends on the effect of suppression of gastric secretion thereof.

EXAMPLE 8

Improvement of blood stream by the present compound (8-1) Test by India ink method Groups of rats loaded with a stress by immersion into water were subjected to laparotomy under etherization, and an India ink (a black writing fluid) was injected into the thoracic aorta. Just after the injection, the stomach was extirpated and after quickly freezing the stomach in a dry ice-acetone bath, the frozen stomach was immersed into methyl salicylate to obtain a transparent specimen of the stomach, the specimen being observed under an optical microscope to examine the image of blood stream in the gastric mucous membrane. In the operation, each of the compounds to be tested was orally administered 30 minutes before immersion of the rat into water at a dose rate of 200 mg/kg body weight.

As the results, the specimen taken from a control animal not administered with the present compound showed an image of stoppage of the blood stream on the mucosal surface, i.e., a typical state of ischemia, and on the contrary, the specimen taken from any animal administered with each of the present compounds showed an image of extremely favorable state of the blood stream not at all different from the image of the specimen taken from the normal rat not loaded with the stress.

(8-2) Test of gaseous hydrogen clearance

In accordance with the method of Semb et al. (1979), the blood stream in the gastric mucous membrane was determined by the method of gaseous hydrogen clearance.

Groups of rats anesthesized by pentobarbital sodium were subjected to laparotomy and a wire-type platinum electrode was fixed on the gastric mucous membrane of the rat. After connecting the electrode to a tissue-blood flow meter by gaseous hydrogen clearance (manufactured by Unique Medical Company, Japan), a predetermined volume of gaseous hydrogen was supplied to the rat by inhalation, and then the curve of washing out the gaseous hydrogen was obtained. From the curve, the amount of blood stream was obtained by the formula of Kety.

In the present test, rats administered with reserpine were used as the model of impairment of blood stream. Namely, upon administering 5 mg/kg of reserpine to a rat intraperitoneally, the amount of blood stream of the rat was reduced to cause the impairment of blood stream, and then, in the case where 50 mg/kg of 2-(2,3-dimethoxyphenyl)-4-thiazolidone, one of the present compounds, was intravenously administered to the thus-treated rat, the blood stream began to increase and returned to the normal state. Each of the present compounds, although there was a difference between their effects, showed the same tendency of restoring the once impaired blood stream.

As has been stated, the cause of peptic ulcer has not been fully elucidated, however, it has been verified by numerous experiments that the unbalance between the acid in the stomach as the aggressive factor and the resistibility of the gastric mucosa as the defensive factor is an important element causing the peptic ulcer.

Accordingly, the fact that the present compound shows the effect of suppressing the gastric secretion and in the same time shows the effect of improving the blood stream in the gastric mucosa, which most deeply concerns the nutrient supply to the gastric mucosa indicates that the present compounds are highly suitable as the therapeutic medicine for peptic ulcer.

Manufacture of the medicinal preparations containing one of the present compounds as an active ingredient

EXAMPLE 9

Manufacture of the granular preparation for oral administration:

To 200 g of finely pulverized compound according to the present invention, 800 g of corn-starch was admixed, and 80 ml of water containing 3 g of dissolved sodium carboxymethylcellulose was added to the mixture. The whole mixture was well kneaded and extruded by an extruding pelletizer to be granular shape. The shaped mixture was dried at a temperature of 60° to 80° C. and screened to obtain granular preparation.

What is claimed is:

1. A 2-substituted-4-thiazolidone of the formula:

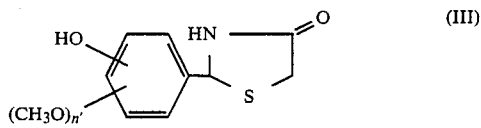

wherein n' is an integer of 1 to 2.

2. A pharmaceutical composition in dosage unit form comprising
a dosage effective for the treatment of peptic ulcer of a 2-substituted-4-thiazolidone of the formula:

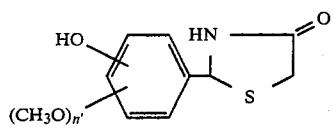

wherein n' is an integer of 1 or 2, and
a pharmaceutically acceptable carrier.

3. A process for producing 2-substituted-4-thiazolidone represented by the general formula (I):

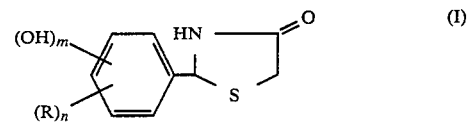

wherein R represents methoxy-, ethoxy-, carboxyl-, methylenedioxy- or dimethylamino-, n is an integer of 1 to 3, and m is 0 or 1 comprising the steps of:
(a) reacting a compound represented by the general formula (IV):

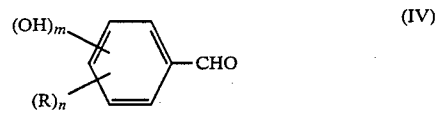

wherein R, n and m represent the same as in the formula (I), with mercaptoacetic acidamide at a temperature of 10° to 50° C. to form an intermediate represented by the general formula (V):

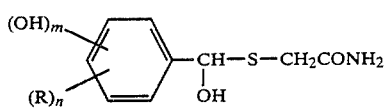

(V)

wherein R, n and m represent the same as in formula (I);

(b) successively subjecting intermediate (V) to cyclization at a temperature of 50° to 150° C. thereby obtaining a compound according to formula (I).

* * * * *

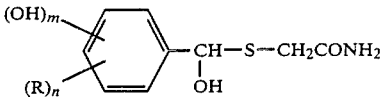

(V)

wherein R, n and m represent the same as in formula (I);

(b) successively subjecting intermediate (V) to cyclization at a temperature of 50° to 150° C. thereby obtaining a compound according to formula (I).

* * * * *